(12) United States Patent
Sanceau et al.

(10) Patent No.: US 6,749,846 B1
(45) Date of Patent: Jun. 15, 2004

(54) INTERFERON-BETA USE IN THE TREATMENT OF EWING'S FAMILY OF TUMORS

(75) Inventors: Josiane Sanceau, Villejuif (FR); Jeanne Wietzerbin, Antony (FR)

(73) Assignees: Institut National de la Sante et de la Recherche Medicale (INSERM), Paris (FR); Institut Curie, Paris (FR)

( * ) Notice: Subject to any disclaimer, the term of this patent is extended or adjusted under 35 U.S.C. 154(b) by 0 days.

(21) Appl. No.: 09/958,274

(22) PCT Filed: Apr. 10, 2000

(86) PCT No.: PCT/EP00/04171
§ 371 (c)(1), (2), (4) Date: Oct. 9, 2001

(87) PCT Pub. No.: WO00/61172
PCT Pub. Date: Oct. 19, 2000

(30) Foreign Application Priority Data

Apr. 9, 1999 (FR) .............................................. 99 04480

(51) Int. Cl.$^7$ ........................ A61K 38/19; A61K 38/16; A61K 35/12; A01N 1/02; G01N 33/53
(52) U.S. Cl. ................ 424/85.1; 424/198.1; 424/277.1; 435/2; 435/7.1; 436/500
(58) Field of Search ............... 436/500; 435/2, 435/7.1; 424/85.1, 198.1, 277.1

(56) References Cited

PUBLICATIONS

Tanaka S et al Neurol Med Chir (Tokyo) 1995 Feb.; 35(2):82–6.*

Byhardt et al J. Interferon Cytokine Res 1996 Nov.; 16(11):891–902.*

Kase S et al Anticancer Res 1993 Mar.–Apr.; 13(2):369–73.*

Kito M et al Biochemical and Biophysical Res Comm 1999; 257:771–776.*

* cited by examiner

Primary Examiner—Larry R. Helms
Assistant Examiner—Christopher Yaen
(74) Attorney, Agent, or Firm—Stites & Harbison PLLC; B. Aaron Schulman

(57) ABSTRACT

The invention relates to the use of interferon-beta for the treatment of Ewing's family of tumors in mammals. A method for treating Ewing's family of tumors in a mammal comprising administering to the mammal in need of such treatment a therapeutically effective amount of interferon-beta is disclosed. The present invention further relates to pharmaceutical compositions suitable for administration to a mammal for the treatment of Ewing's family of tumors comprising interferon-beta in a therapeutically effective amount, together with a pharmaceutically acceptable carrier.

18 Claims, 6 Drawing Sheets

INTERFERON-BETA USE IN THE TREATMENT OF EWING'S FAMILY OF TUMORS

The invention relates to the use of interferon-beta for the treatment of Ewing's family of tumors in mammals.

The family of Ewing's tumors represents the second most common type of bone tumors observed in children after osteosarcoma. The family includes Ewing's sarcoma (EWS or Ewing's tumor of bone), extraosseus Ewing's (EOE), primitive neuroectodermal tumors (PNET or peripheral neuroepithelioma) and Askin's tumors (PNET of the chest wall). These tumors are rare diseases in which malignant cells are found in the bone and soft tissues, and recent protocols use the same treatment for this family of tumors. EWS is mostly observed in adolescent and young adults, and the most common sites for the primary lesion are the pelvic bones, femur, humerous and ribs. Incidence of Ewing's sarcoma is estimated to be about 60% of the Ewing's family of tumors.

Studies using immunohistochemical markers, cytogenetics, molecular genetics, and tissue culture indicate that these tumors are all derived from the same primordial stem cell. Cytogenetic studies of the Ewing's family of tumors have identified a consistent alteration of the EWS locus on chromosome 22 band q12 that may involve other chromosomes, including 11 or 21. Characteristically, the amino terminus of the EWS gene is juxtaposed with the carboxy terminus of another chromosome. In the majority of cases (90%), this chromosomal translocation directs the fusion of the 5' end of the EWS gene, encoding a protein capable of participation in RNA metabolism, with the 3' end of the Fli-1 gene, a member of the Ets transcription factor family located on chromosome 11 band q24 (Delattre et al., *Nature* 359:162–165 (1992)). Several fusion genes can be generated according to the cleavage sites (between exons 7 and 11 of EWS and exons 3 to 9 from Fli-1).

The more frequent fusion, EWS-Fli-1 type I, fuses EWS exon 7 with Fli-1 exon 6 and represents 50% of cases. The type II fusion (25% of cases) ligates EWS exon 7 with Fli-1 exon 5. In addition to these two principal fusion types, about ten other combinations have been described.

In certain Ewing's tumor cases, EWS is not fused to Fli-1 but to another member of the Ets family, e.g. FEV. Other Ets family members which may combine with the EWS gene are ERG (located on chromosome 21), ETV (located on chromosome 7), and $E_rAF$ (located on chromosome 17), which result in the following translocations: t(21;22), t(7;22), and t(17;22) respectively.

These genetic alterations reach a constant biochemical consequence: Ewing cells always express a chimeric protein bearing the N-terminal region of EWS fused to a DNA binding domain of the Ets protein family. This constancy suggests that this fusion exerts a central role in Ewing's tumor development.

In Ewing's sarcoma, the role of the EWS/Fli-1 fusion protein has been experimentally demonstrated. This protein can transform mice fibroblasts, and these cells are able to generate tumors in nude mice.

From in vitro experiments, it was shown that the EWS/Fli-1 protein was able to activate certain gene transcription more efficiently than Fli-1. This fact suggests that the EWS/Fli-1 protein fusion exerts its oncogenic actions through the abnormal activation of certain cellular genes.

It was also shown that the PU-1 protein, also from the Ets family, is implicated in the control of interferon and cytokine regulated gene expression (Perez et al., *Mol. Cell Biol.* 14:5023–5031 (1994)).

Important prognostic factors for the Ewing's family of tumors include the site and volume of the primary tumor and whether the disease is metastatic. Size of the tumor is also thought to be an important variable. With current treatment, studies suggest that 50%–70% of patients without metastatic disease have a long-term disease-free survival, compared to only 20%–30% for patients who present with metastatic disease. As such, there remains an acute need in the art for an effective method of treating the Ewing's family of tumors.

Accordingly, the present invention provides an effective method of treating the Ewing's family of tumors in a mammal. Other features and advantages of the present invention will be set forth in the detailed description of preferred embodiments that follows, and in part will be apparent from the description or may be learned by practice of the invention. These advantages of the invention will be realized and attained by the compositions and methods particularly pointed out in the written description and claims hereof.

Rosolen et al. (*Modern Pathology*, 1997, 10:55–61) reported that the treatment of a cell line derived from Ewing's sarcoma with interferon-alpha, induces an inhibition of cell growth in vitro.

The authors of the present invention have now shown that interferon-beta (IFN-β) which binds the same receptor as interferon-alpha (IFN-α) but which is known to exert distinct activities (Runkel et al., 1998, the Journal of Biological Chemistry, 14:8003–8008), exhibits an antiproliferative action on Ewing's sarcoma.

They have more particularly shown that the antiproliferative action of IFN-β on cells derives from Ewing's sarcoma in vitro was distinctly superior than the one of IFN-α.

Therefore, one embodiment of the present invention is directed to a method of treating Ewing's family of tumors in a mammal comprising administering to a mammal in need of such treatment a therapeutically effective amount of IFN-β. A second embodiment of the present invention is directed to a composition suitable for administration to a mammal for the treatment of Ewing's family of tumors comprising IFN-β in a therapeutically effective amount, together with a pharmaceutically acceptable carrier.

It is to be understood that both the foregoing general description and the following detailed description are exemplary and explanatory only and are intended to provide further explanation of the invention as claimed.

Unless defined otherwise, all technical and scientific terms used herein are intended to have the same meaning as is commonly understood by one of ordinary skill in the relevant art.

As used herein, the term "Ewing's family of tumors" means a type of tumor found in bone and soft tissues characterized by small round cells and associated with an alteration of the EWS locus on chromosome 22. The family of tumors includes Ewing's sarcoma (Ewing's tumor of bone or ETB), extraosseus Ewing's (EOE), peripheral primitive neuroectodermal tumors (PNET or peripheral neuroepithelioma) and Askin's tumors (PNET of the chest wall).

The individual cells of Ewing's sarcoma and EOE contain round to oval nuclei with fine dispersed chromatin without nucleoli. Occasionally, cells with smaller, more hyperchromatic (and probably degenerative) nuclei are present giving a "light cell-dark cell" pattern. The cytoplasm varies in amount, but in the classic case it is clear and contains glycogen, which can be highlighted with a periodic acid-Schiff (PAS) stain. The tumor cells are tightly packed and grow in a diffuse pattern without evidence of structural is organization.

The histologic appearance of the PNET differs somewhat from Ewing's sarcoma and EOE. These tumors are typically composed of round to ovoid hyperchromatic cells with minimal cytoplasm. The tumor cells are typically arranged in nests and trabeculae with variable rosette formation. The rosettes may have a central lumen, but are often ill-defined, composed of tumor cells arranged around an empty space. The classic lobular growth pattern is best appreciated at low-power, and differs from the typical diffuse growth seen in EOE. Occasionally, groups of cytologically uniform, round cells with dispersed chromatin resembling those in EOE are seen interspersed in an otherwise typical PNET. This overlap of features lends confidence to the concept that these tumors are indeed the same tumor with a spectrum of differentiation.

As used herein, the term "mammal" indicates any mammalian species, and includes, but is not limited to, rabbits, mice, dogs, cats, primates and humans, preferably humans. As used herein, the term "treatment" refers to any process, action, application, therapy, or the like, wherein a mammal, including a human being, is subject to medical aid with the object of improving the mammal's condition, directly or indirectly. In the context of tumor growth or tumor cell growth, "treatment" includes, but is not limited to, inhibition and prevention.

As used herein, the term "inhibition" can be assessed by the delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition is referred to herein as prevention.

As used herein, the term "prevention" means no tumor or tumor cell growth if none had occurred, and no further tumor or tumor cell growth if there had already been growth.

As used herein, the term "therapeutic treatment" indicates treating a subject after a disease is contracted, and includes prophylactic therapy.

As used herein, the term "effective amount" signifies an amount effective to perform the function specified. A "therapeutically effective amount," in reference to the treatment of a tumor, refers to an amount sufficient to bring about one or more or the following results: reduce the size of the tumor, inhibit the metastasis of the tumor, inhibit the growth of the tumor, prevent the growth of the tumor, relieve discomfort due to the tumor, or prolong the life of a patient inflicted with the tumor.

As used herein, the term "interferon" means the family of highly homologous cytokine proteins and glycoproteins which are known to have various biological activities, such as antiviral, antiproliferative and immunomodulatory activity at least in the species of animal from which such substances are derived.

At present, the interferons are categorized into five different types: alpha IFN (leukocyte IFN), beta IFN (fibroblast IFN), gamma IFN (immune IFN), omega IFN and tau IFN (trophoblastic factor). For a review of the details and homology relationships of the known IFN proteins, see. e.g., Viscomi, *Biotherapy* 10:59–86 (1997).

As used herein, the terms "interferon-beta" and "IFN-β" include all proteins, polypeptides and peptides which are natural or recombinant IFN-β's or derivatives thereof, and which are characterized by the biological activity of those IFN-β's against malignant, non-malignant or viral diseases. These include IFN-β-like compounds from a variety of sources such as natural IFN-β's (human and non-human), recombinant IFN-β's and synthetic or semi-synthetic IFN-β's.

As used herein, the term "recombinant interferon-beta" refers to IFN-β produced by recombinant DNA techniques, i.e., produced from cells to transformed by an exogenous DNA construct encoding the desired IFN-β polypeptide.

As used herein, the term "International Unit" means the internationally established potency unit of measurement of IFN as defined by the International Conference for Unification of Formulae and as recognized by those of skill in the art.

As used herein, the term "pharmaceutically acceptable carrier" refers to a diluent, adjuvant, excipient, or vehicle with which the therapeutic is administered. It includes any and all solvents, dispersion media, aqueous solutions, coatings, antibacterial and antifuincgal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated.

Supplementary active ingredients can also be incorporated into the compositions of the invention. A composition is said to be "pharmacologically acceptable" if its administration can be tolerated by a recipient patient.

As used herein, "simultaneous or sequential" is meant that IFN-β is co-administered with another cytokine or chemotherapeutic agent or together with radiotherapy or surgery or where IFN-β administration is preceded or followed by non-IFN-β treatment. Where "sequential" therapy is occurring, the time difference between IFN-β administration and non-IFN-β treatment can be minutes, hours, days, weeks or months depending on the tumor or sarcoma being treated, the mammal being treated and the effectiveness of the overall treatment.

The term "substantially simultaneously" means "at about the same time" with the only limitation being that both substances must be present together at the tumor site.

In accordance with the present invention, it has been discovered that IFN-β can significantly inhibit and/or prevent tumor growth in Ewing's sarcoma. As such, in one aspect of the invention there is provided a method of treating Ewing's family of tumors in a mammal comprising administering to the mammal in need of such treatment a therapeutically effective amount of IFN-β.

In a preferred embodiment, the IFN-β is recombinant IFN-β. For example, recombinant IFN-β1a, (such as the one commercialized as REBIF® by Ares-Serono or AVONEX® by Biogen, which are glycosylated recombinant IFNs produced in mammal cells, or IFN-β1b (such as the one commercialized under the name of BETASERON® by Schering AG or BETAFERON® by Berlex/Chiron) can be used. More preferably, glycosylated recombinant IFN-β1a is utilized.

An extracted natural IFN-β can be used in the present invention as well such as the one commercialized under the name of FRONE® by Ares-Serono. Natural human IFN-β can be purified from several cell sources including leukocytes isolated from whole blood, neonatal fibroblasts, lymphoblastoid and various leukemic cell lines. IFN-β can also be a mammalian extract such as ruminant or bovine IFN-β. As such, the IFN-β employed can be "homologous" to the mammal to be treated meaning that it has the same origin as the species of mammal to be treated (e.g. human IFN-β for treatment of a human or murine IFN-β for treatment of a mouse) or can be "heterologous" to the mammal to be treated meaning that the species origin of IFN-β and the species of the mammal are different (e.g. human IFN-β for treatment of a mouse or murine IFN-β for treatment of a human).

The IFN-β of the inventive method also includes, for example, known sequences and those variants whose genes are characterized by a high degree of homology with the known sequence and which code for biologically active IFN-β and compounds having substantially the same biologically activity as known forms of IFN-β. The IFN-β can also contain single or multiple amino acid insertions, deletions and/or additions to the naturally occurring sequence and may be fragmented to a part carrying the active site of IFN-β.

In general, any IFN-β molecule is encompassed by the present invention and is included in the expression "IFN-β" provided all such molecules have the effect of preventing or reducing the size of Ewing's family of tumors in vitro, in a laboratory test animal in vivo or in a mammal to be treated.

The present invention is exemplified by the effect of IFN-β against Ewing's sarcoma tumors in mice. It is to be understood, however, that the present invention extends to the in vivo effects of IFN-β in all mammals such as humans, and to all of Ewing's family of tumors. In a preferred embodiment, the mammal is human. Exemplary non-human mammals include livestock animals such as cows, pigs, sheep, horses, goats, companion animals such as cats and dogs, and laboratory test animals such as mice, rabbits, guinea pigs or hamsters.

According to the present invention, the IFN-β can be administered by any suitable route such as oral or parenteral, i.e., any route other than the alimentary canal. In a preferred embodiment, the parenteral administration is by intravenous (within or into a vein), intramuscular (within a muscle), subcutaneous (introduced beneath the skin) or percutaneous (effected through the skin) means. A systematic injection is preferred wherein IFN-β enters the blood stream, but a direct injection in the tumor itself can also be advantageously used.

Administration can be as a single dose or repeated doses one or more times after a certain period. When administering IFN-β by injection, the administration may be by continuous injections, or by single or multiple boluses. The administration modes and posology can be determined by those skilled in the art according to criteria generally considered for a therapeutical treatment adapted to a patient. As such, dosage of the administered agent will vary depending upon such factors as the patient's age, weight, height, sex, general medical condition, previous medical history, etc.

The effective amount of IFN-β will depend on the mammal and the condition to be treated. In general, it is desirable to provide the recipient with a dosage which is in the range of about $1 \times 10^6$ to about $90 \times 10^6$ International Units (IU), although a lower or higher dosage may be administered. Preferably, a dose of in the range of about $1 \times 10^6$ to about $45 \times 10^6$ IU can be administered. Skilled practitioners will adjust the timing and dosage to fit the clinical symptoms of the patients. Such knowledge has been accumulated over decades and is reported in the medical literature. The IFN-β composition may be administered alone or formulated with pharmaceutically acceptable carriers, in either single or multiple doses. As such, in another embodiment of the invention the IFN-β is administered as part of a pharmaceutical composition comprising a pharmaceutically acceptable carrier.

Suitable pharmaceutical carriers include, but are not limited to, inert solid diluents or fillers, sterile aqueous solutions, and various nontoxic organic solvents. Pharmaceutically acceptable carriers should be inert. Further, the carrier should not react with or otherwise reduce the effectiveness of the active ingredients, and more particularly, should not significantly diminish the effectiveness or stability of the IFN-β. Pharmaceutically acceptable carriers include water, ethanol, polyethylene glycol, mineral oil, petrolatum, propylene glycol, lanolin, and similar agents.

The pharmaceutical forms suitable for injectable use include sterile aqueous solutions (where water soluble) or dispersions and sterile powders for the extemporaneous preparation of sterile injectable solutions or dispersion. In all cases the form should be sterile and should be fluid to the extent that easy syringability exists. It should also be stable under the conditions of manufacture and storage and be preserved against the contaminating action of microorganisms such as bacteria and fungi.

The IFN-β composition can be administered alone or can be simultaneously or sequentially administered in combination with any pharmaceutical agent, such as another agent efficient against Ewing's sarcoma. In this "combined therapy", IFN-β can be administered with other cytokines and/or chemotherapeutic agents and/or radiotherapeutic protocol and/or with surgery. Such cytokines include, but are not limited to, interleukin-1, TNF-α, IFN-α, and/or interferon-gamma. Representative chemotherapeutic agents are well known in the art and include, but are not limited to, Doxorubicin, Actimomycin, Cyclophosphamide (VAdriaC), Etoposide, Ifosfamide and Vincristine.

More particularly the authors of the present invention have shown a synergic effect resulting from an associated treatment of IFN-β and Ifosfamide.

Amounts of other cytokines will be similar to the effective amounts of IFN-β. The effective amounts of chemotherapeutic agents will vary as depending on the agent and are known in the art. The subject compositions may be administered either in conjunction with the second treatment modalities, or separately, e.g. at different times or in different syringes or tablets.

Surgery may be used in certain cases to try to remove the cancer and some of the tissue around it. Surgery may also be used to remove any tumor that is left after chemotherapy or radiation therapy. In a preferred embodiment, the IFN-β composition is administered in combination with surgical therapy, preferably after the surgical operation.

Another aspect of the present invention further comprises the substantially simultaneous or sequential administration of one or more other cytokines, derivatives thereof and/or one or more chemotherapeutic agents and/or the simultaneous or sequential treatment by radiotherapy. Accordingly, IFN-β can be co-administered with another cytokine or chemotherapeutic agent or together with radiotherapy or where IFN-β administration is preceded or followed by non-IFN-β treatment. Where "sequential" therapy is occurring, the time difference between IFN-β administration and non-IFN-β treatment may be minutes, hours, days, weeks or months depending on the tumor or sarcoma being treated, the mammal being treated and the effectiveness of the overall treatment.

The present invention further relates to the use of IFN-β or active fragment, mutant or derivative thereof alone or together with one or more other cytokines and/or chemotherapeutic agents in the manufacture of a medicament for the treatment of patients carrying tumors or sarcomas from the Ewing's family of tumors.

The present invention also relates to a process for preparing the abovementioned pharmaceutical composition characterized by mixing, according to known methods, active ingredients with acceptable excipients which are pharmaceutically acceptable.

In all of the above cases, the present invention also extends to the use of derivatives of IFN-β and derivatives of other cytokines and/or chemotherapeutic agents. By "derivative" is meant recombinant, chemical or other synthetic forms of IFN-β or other cytokine or chemotherapeutic agent and/or any alteration such as addition, substitution and/or deletion to the amino acid sequence component of the molecule, provided the derivative possesses the ability to prevent and/or inhibit Ewing's family of tumors.

The present invention further extends to a pharmaceutical composition comprising IFN-β and/or its derivatives alone or in combination with one or more other cytokines and/or their derivatives and/or chemotherapeutic agents and one or more pharmaceutically acceptable carriers and/or diluents.

The authors of the present invention have also established that IFN-β mediates apoptosis via induction of IRF-β and activation of caspase-7.

These results provide a foundation for a method for monitoring the sensitivity of Ewing's sarcoma cells to IFN-β-mediated apoptosis, by following the expression and/or proteolyzed activation of caspase-7. This method can be particularly advantageous to assess the sensitivity of a patient toward a treatment with IFN-β, for example by analyzing surgical samples of Ewing's tumors.

This analysis of activation of caspase-7 can be carried out by any standard method well-known by one skilled in the art.

An inmunoassay of caspase-7 by means of an antibody directed against this protein is preferred.

However, one can also detect and/or quantify the mRNA coding for this caspase, for example.

All patents and publications cited in this disclosure are indicative of the level of skill of those skilled in the art to which this invention pertains and are all herein incorporated by reference in their entirety.

Having now generally described the invention, the same will be more readily understood through reference to the following Examples which are provided by way of illustration, and are not intended to be limiting of the present invention, unless specified.

EXAMPLES

Example 1

Figure 1:
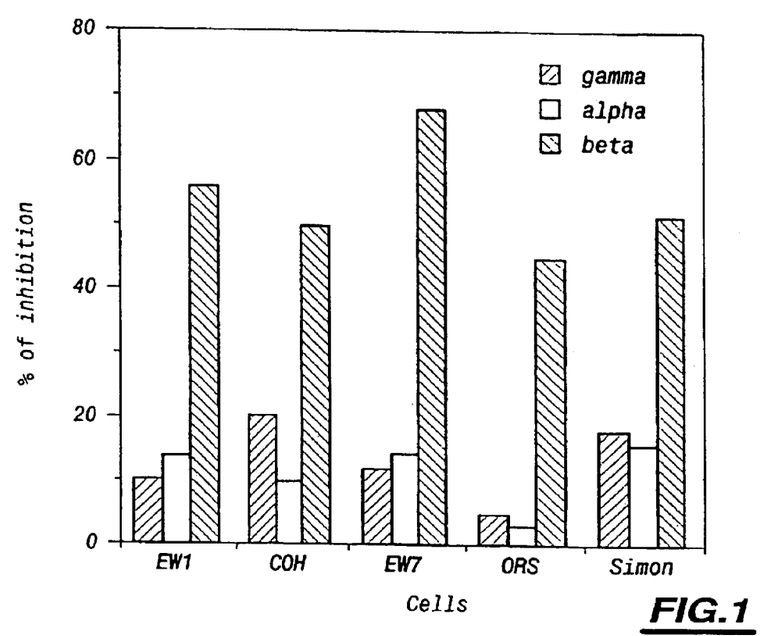
FIG. 1 represents the percentage of growth inhibition of cell lines treated with IFN-α, β or γ, at the same concentration.

Antiproliferative Activity of β-interferon on Cells Derived from Ewing Tumors. Study in Vitro α- and β-interferons (IFNs) (termed type I) and γ-IFN (type II) are used for their antiproliferative activity on 5 cell lines derived either from primary Ewing tumors (before any treatment: EW-7, COH), or metastasized recidivations (EW-1, ORS, Simon) (FIG. 1).

The EW1 line is a sarcoma line of the $8^{th}$ right rib. This line is derived from a pleural effusion (metastases) (exon 7 of EW/exon 5 of Fli) (Melot et al., *Hybridoma*, 1997, No. 16, page 457).

The COH line is a tumour line of the knee with pulmonary metastases. This line is derived from the primary tumor before chemotherapy (exon 10 of EW/exon 6 of Fli) (Melot et al., *Hybridoma*, 1997, No. 16, page 457).

The EW7 line is a tumor line of the scapula. This line is derived from the primary tumor before chemotherapy (exon 7 of EW/exon 6 of Fli).

The ORS line is a cell line derived from a secondary tumor (metastases) (Melot et al., *Hybridoma*, 1997, No. 16, page 457).

The SIMON line is also a cell line derived from a secondary tumor (metastases).

Regardless of the cell line used, the 24- or 48-hour treatment with γ-IFN or with α-IFN (400 units/ml) results in a low inhibition of cell growth, 10 to 25%.

Treatment with β-IFN (REBIF®, glycosylated recombinant IFN-β1a 400 units/ml) is more effective than treatment with α-IFN or γ-IFN, because it leads, after 24 hours of activation, to an inhibition of growth which is higher than 50% regardless of the cell line used, with for example an inhibition of 70% on the EW-7 line (cf. FIG. 1).

Figure 2:
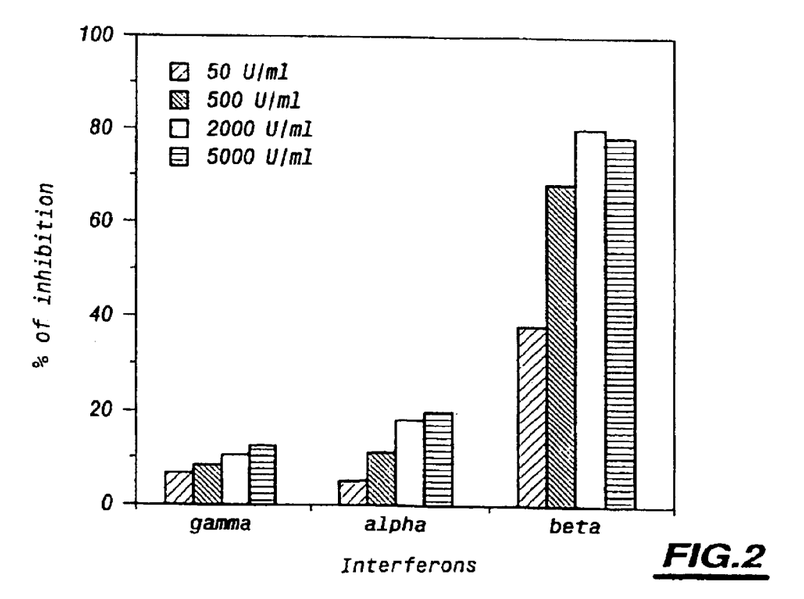
FIG. 2 represents the percentage of growth inhibition of EW-7 cells treated with increasing doses of IFN-α, β or γ.

As shown in FIG. 2, this difference in antiproliferative activity between the three IFNs does not depend on the dose of IFN used. The EW-7 cells are selected in order to measure the antiproliferative effect on increasing doses of IFNs, from 50 units/ml to 5000 units/ml. In general, regardless of the IFN dose used, the inhibition of growth after addition of β-IFN is much higher than the effect observed after addition of α-IFN or γ-IFN: from 40 to 80% inhibition for β-IFN against 6 to 10% and 6 to 20% for γ-IFN and α-IFN respectively. It may be noted that the addition of β-IFN at 500 units/ml gives practically the maximum antiproliferative response.

The differential effects observed between the two IFNs might be the consequence of a difference in the mechanism of activation of genes induced by the IFNs and involved in their antiproliferative effect, such as the genes encoding 2'5'oligo(A)-synthetase or IRF-1 (Interferon Regulatory Factor 1).

Example 2

Antiproliferative Action of IFN-β on the Growth of Ewing's Tumors. In Vivo Study is Nude Mice A. Malignant Cell Injection Solid tumors were generated by subcutaneous injection of 20×10⁶ EW7 cells (shoulder-blade tumor derived cell line) from primary tumor before chemotherapy (EW exon 7/Fli exon 6) in 6 week-old nude mice.

After ten days, two groups of five mice each were constituted, a control mice group and a mice group receiving IFN-β (REBIF®).

Injections were performed in the tumor itself with 5×10⁵ IFN units per mouse, 3 times weekly. Treatment was continued for a 5-week period during which tumor volumes were determined every 3 days.

Figure 3:
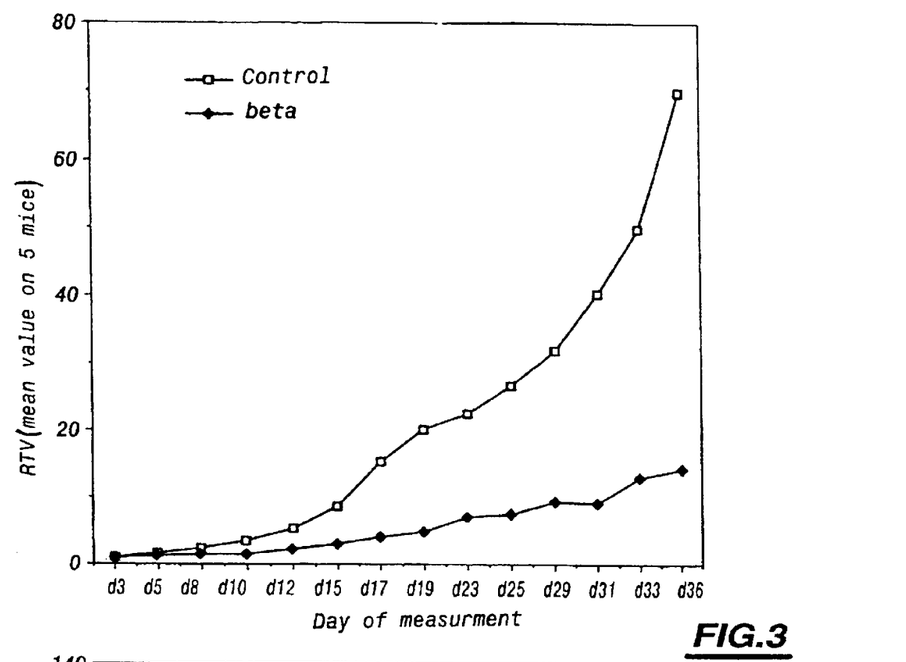
FIG. 3 represents the effect of IFN-β on Ewing's tumor development as generated by subcutaneous injection of EW-7 cells to mice. Relative tumor volumes (RTV) are measured on a time dependent manner.

Relative tumor volumes (RTV) demonstrate slower tumor growth after IFN-β injection. FIG. 3 constructed from RTV average dates shows a very sharp decrease of turnover growth rates after IFN-β injection.

These results from established tumors in the experimental growth phase permit the confirmation of in vitro results with cell lines.

B. Solid Tumor Graft

A second experiment was performed in vivo in 8-week old nude mice. A tumor sample 5 mm in diameter from a solid tumor developed in a nude mouse after 20×10⁶ EW7 cells injections, conserved by in vivo transfer, was grafted in nude mice.

Three days after grafting, two groups of 12 mice each were constituted, a control group receiving phosphate buffer solution (PBS) injections and a group receiving IFN-β injections. 1×10⁶ units of IFN-β was injected in tumor sites in a 5 days-a-week manner (Monday through Friday) for 1 month.

Figure 4:
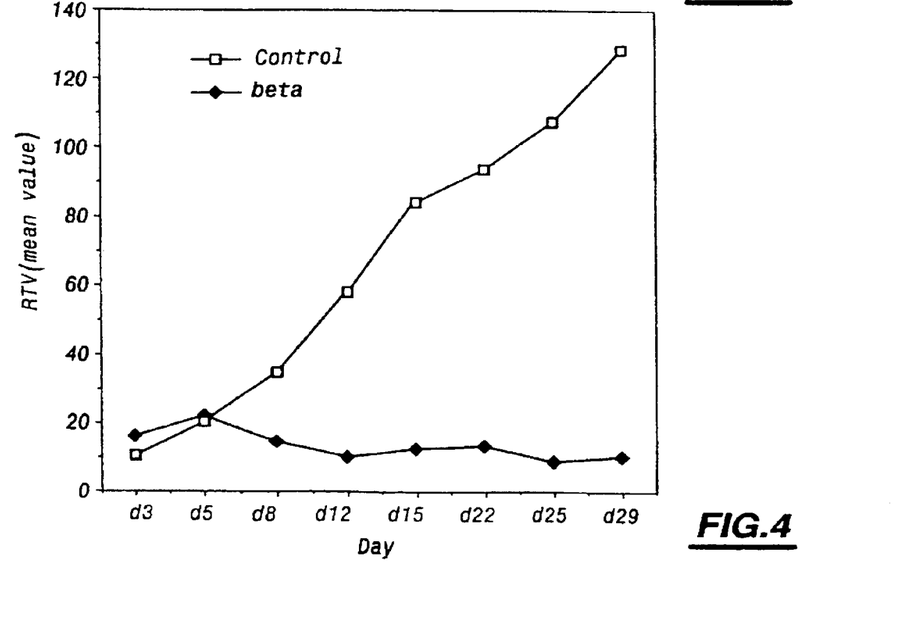
FIG. 4 displays a growth rate plot of the Ewing's tumors grown in nude mice after IFN-β injection. The average value of relative tumor volumes (RTV) of 12 mice is represented.

The tumor growth curves were determined after measuring grafted tumor diameters in each mouse twice a week (FIG. 4).

Figure 5:
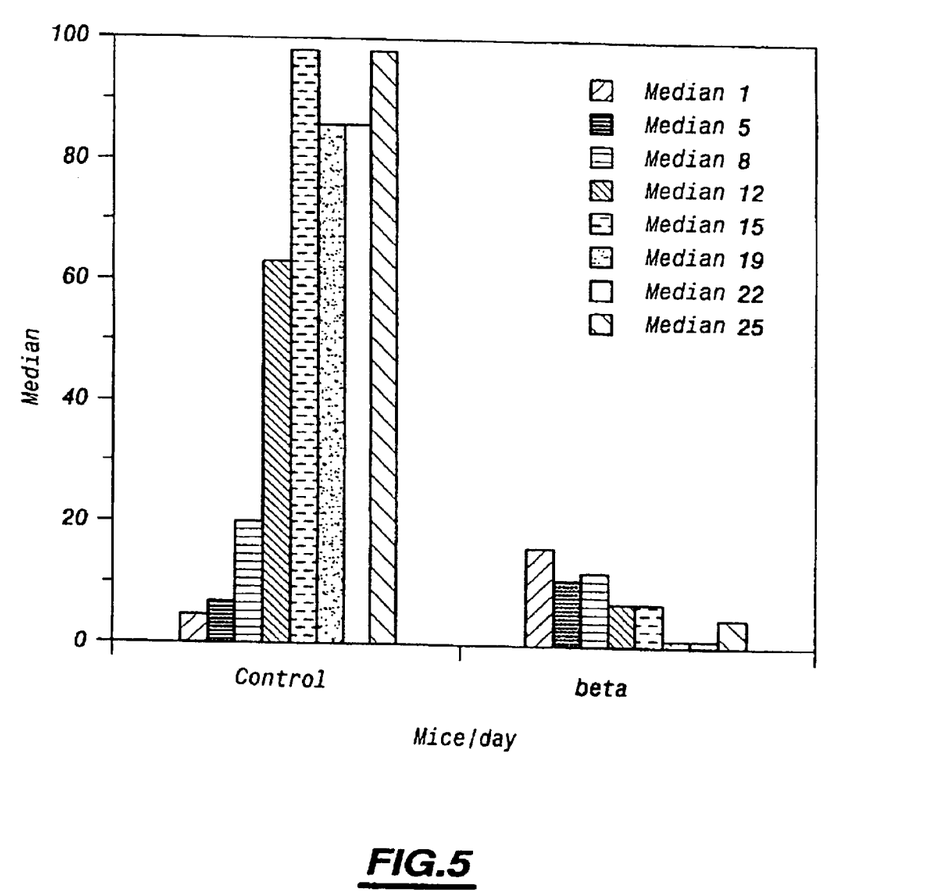
FIG. 5 represents the effect of IFN-β on Ewing's tumors grown in nude mice. Tumor volumes were determined twice a week for each group, and the volume median was determined.

FIG. 4 shows the plots obtained from average RTV for each 12 mice group. An almost linear progression of tumor development in control mice was observed, while tumor proliferation was practically null in grafts receiving IFN-β. This result was confirmed by median calculation for each group (FIG. 5).

It is worth noting that one month after the interruption of IFN injection, 40% of the mice which had received IFN-β did not develop tumors.

In view of the foregoing description taken with the Examples, those skilled in the art will be able to practice the invention in various enablements and embodiments without departing from the spirit and scope of the invention as defined in the appended claims.

Example 3

Effect of IFN-β on the Expression of IRF-1 in Ewing's Sarcoma Derived Cell Lines To investigate IRF-1 gene expression and regulation by IFN-β, the authors of the invention assessed IRF-1 gene expression by reverse-transcription polymerase chain reaction (RT-PCR). Total RNAs extracted 3, 6 and 18 hours after treatment with IFN-β demonstrated that IRF-1 specific mRNA was induced by IFN-β. In EW-7 cells, IFN-β induced IRF-1 gene expression in a time-dependent manner for up to 6 hours of stimulation. However, after stimulation by IFN-β, IRF-1 mRNA was still detectable at 18 hours. Similar results were obtained for the three other ES cell lines, but with different levels of IRF-1 gene induction.

Example 4

Figure 6:
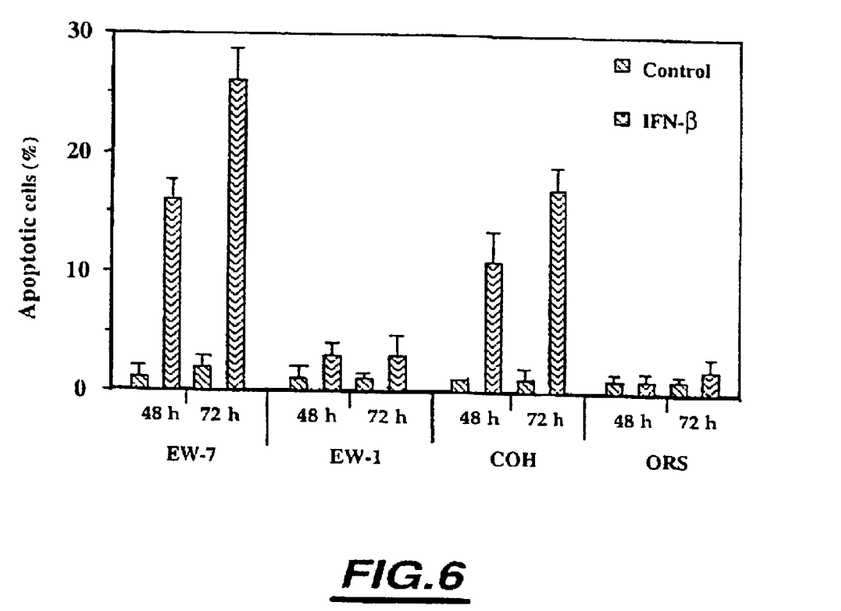
FIG. 6 represents the quantification of apoptotic cells in cell lines derived from Ewing's sarcoma. The four ES cell lines were stimulated with IFN-β. After 48 and 72 hours, the fragmented nuclei were detected using Hoechst 33258 fluorescent dye on harvested cells. Nuclear fragmentation was evaluated by counting the apoptotic cells in the total populations of untreated and IFN-treated cells respectively. The percentages of apoptotic cells are the means of 3 independent experiments, after two readings by two experimenters, for each of the four cell lines.

Relationship Between IRF-1 Expression and IFN-β Induced Apoptosis in Ewing's Sarcoma Cell Lines The authors of the invention were particularly interested in determining whether stimulation of these ES cell lines by IFN-β provoked apoptosis, and the possible relationship between IRF-1 gene expression. For this purpose, nuclear fragmentation was evaluated by Hoechst staining, and quantified by counting the number of apoptotic cells in the total populations of untreated cells or cells treated with IFN-β for 48 or 72 hours (FIG. 6). EW-7 and COH cells exhibited a time-dependent increase in apoptotic cells after IFN-β treatment, whereas EW-1 and ORS cells underwent no significant apoptosis during either period of IFN-β treatment. The differences in sensitivity of the four ES cell lines to IFN-β-dependent apoptosis, and the correlation between $p21^{WAF-1/Cip-1}$ and Bcl-2 protein levels were analyzed by immunoblot analysis after IFN-β treatment. Down-regulation of total cellular Bcl-2 protein correlated with the upregulation of $p21^{WAF-1/Cip-1}$ and IRF-1 expression in EW-7 and COH cells, whereas no change in Bcl-2 protein expression was observed in EW-1 or ORS cells. The $p21^{WAF-1/Cip-1}$ protein was not detectable in EW-1 or ORS cells, whether or not they were treated with IFNs.

Because induction of apoptosis by cytokines has been shown to involve the expression of caspase genes, the authors of the invention explored the possible enhancement of caspace gene expression in ES cell lines by IFN-β. For this purpose, RNase protection assays were performed for the caspase family using the hApol kit (Pharmingen), after stimulation of ES cells with IFN-β for 18 hours. Expression of caspase-7 mRNA rose significantly in the EW-7 cells stimulated with IFN-β and to a lesser extent the mRNA level of caspase-3 and -8; the mRNA levels of caspases-1, -6 and -9 remained unchanged. Similar results were observed in COH cells. In EW-1 and ORS cells, the mRNA levels of caspases remained unchanged.

Figure 7:
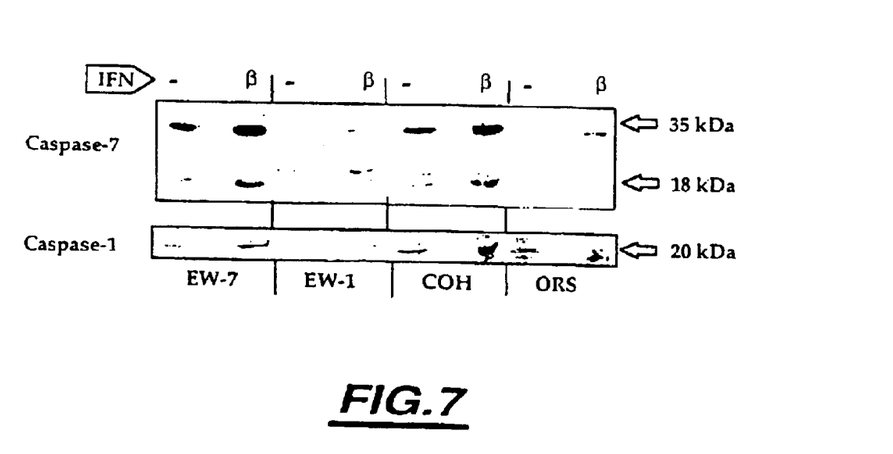
FIG. 7 shows the effects of IFN-β on caspase-1 and caspase-7 expression. EW-7, EW-1, COH and ORS cells were treated for 18 hours with IFN-β. Total cell extracts were submitted to Western blot analysis. Caspase-1 and caspase-7 were successively revealed with specific antibodies.

In view of the RNase protection results, the authors investigated the possibility that IFN-β enhances proteolysis leading to the formation of active caspase subunits. The proteolyzed 20 kDa caspase-1 was first revealed after probing with antibodies, against the active form of caspase-1. After stripping the blot, the 35 kDa and 18 kDa forms of caspase-7 were detected with the specific antibodies against caspase-7 (which are purified mouse antibodies from Pharmingen (Becton Dickinson)). Immunoblot analysis with antibodies against caspase-7 revealed that IFN-β not only increased the amount of procaspase-7 protein but also generated the proteolyzed active subunit of 18 kDa (FIG. 7). These processes were only observed in the wild-type p53 cells EW-7 and COH tumor cells. An increase in the 20 kDa caspase-1 subunit was also observed in EW-7 and COH cells after IFN-β or IFN-β treatment, but was not detectable in EW-1 or ORS cells (FIG. 7). Both the increase in the gene expression of caspase-7 and the cleavage of pro-caspase-7 detected after IFN-β treatment suggest that in cells derived from Ewing's sarcoma, IFN-β triggers cell death by selectively upregulating activated caspase-7.

Example 5

Ectopic Expression of IRF-1

To demonstrate the role of IRF-1 in apoptosis in Ewing's sarcoma cells, the authors of the invention attempted to generate cells expressing IRF-1. ES cell lines constitutively expressing IRF-1 have been difficult to establish because of the strong cytotoxic effects of endogenous IRF-1. Thus, an inducible form of IRF-1 was used to determine whether the induction of IRF-1 enhanced the death of the Ewing's tumor cells that are normally resistant to IFN-β mediated cell death. Consequently, a tetracycline-inducible system was used, utilizing the reverse tTA activator (rtTA) which permits doxycycline (Dox) inducible expression of IRF-1 (Nguyen, H. et al., *Oncogene*, 15:1425–1435 (1997)). Cell clones from rtTA-IRF-1 of all four ES cell lines were expanded individually and screened for IRF-1 expression by Western blot analysis, following 48 hours of growth in medium with or without Dox. Dox stimulation led to induction of IRF-1 protein in the four ES-TA/IRF-1 cell lines, but not in the control rtTA cell lines. To determine whether IRF-1 induction was associated with nuclear fragmentation, cells were stained with Hoechst fluorescent dye after Dox treatment of the transfected cells for 24 or 48 hours. All ES-TA/IRF-1 cell lines; regardless of their p53 status, underwent time-dependent apoptosis after stimulation by Dox. Forty to 50% of the apoptotic cells were detected at 48 hours of Dox stimulation, and almost all the cells had undergone apoptosis by 96 hours after stimulation. Western blot analysis of total extracts of ES-TA/IRF-1 cells showed a correlation between IRF-1 induction by Dox and $p21^{WAF-1/Cip-1}$ upregulation with concomitant downregulation of Bcl 2 protein. An increasing level of the proteolyzed active subunit caspase-7 was also observed in the four ES-TA/IRF-1 cell lines treated with Dox for 48 hours, but not in the control rtTA cell lines. Taken together, these results suggest that caspase-7 is involved in the apoptosis mediated by IRF-1, in Ewing's sarcoma cells.

Example 6

Antitumor Activity of IFN-β on Ewing's Tumor Study in Nude Mice

The aim of this experiment was to study the effect of IFN-β on the development (growth) of an existent Ewing's tumor.

A 5 mm-diameter tumor sample originating from a solid tumor developed in nude mice after injection of $20 \times 10^6$ EW-7 cells and preserved by in vivo transfer was grafted into 8-week-old nude mice. After three weeks, mice which had developed a tumor of approximately 100–200 mm³ were divided into 2 "randomized" groups of 12 mice, the first group receiving PBS as control and the second IFN-β (REBIF®).

IFN-β was injected into the tumor mass itself at a dose of $8 \times 10^5$ units per mouse 5 times weekly (Monday to Friday). Dosing continued for 5 weeks during which tumors were measured every third day.

Figure 8:
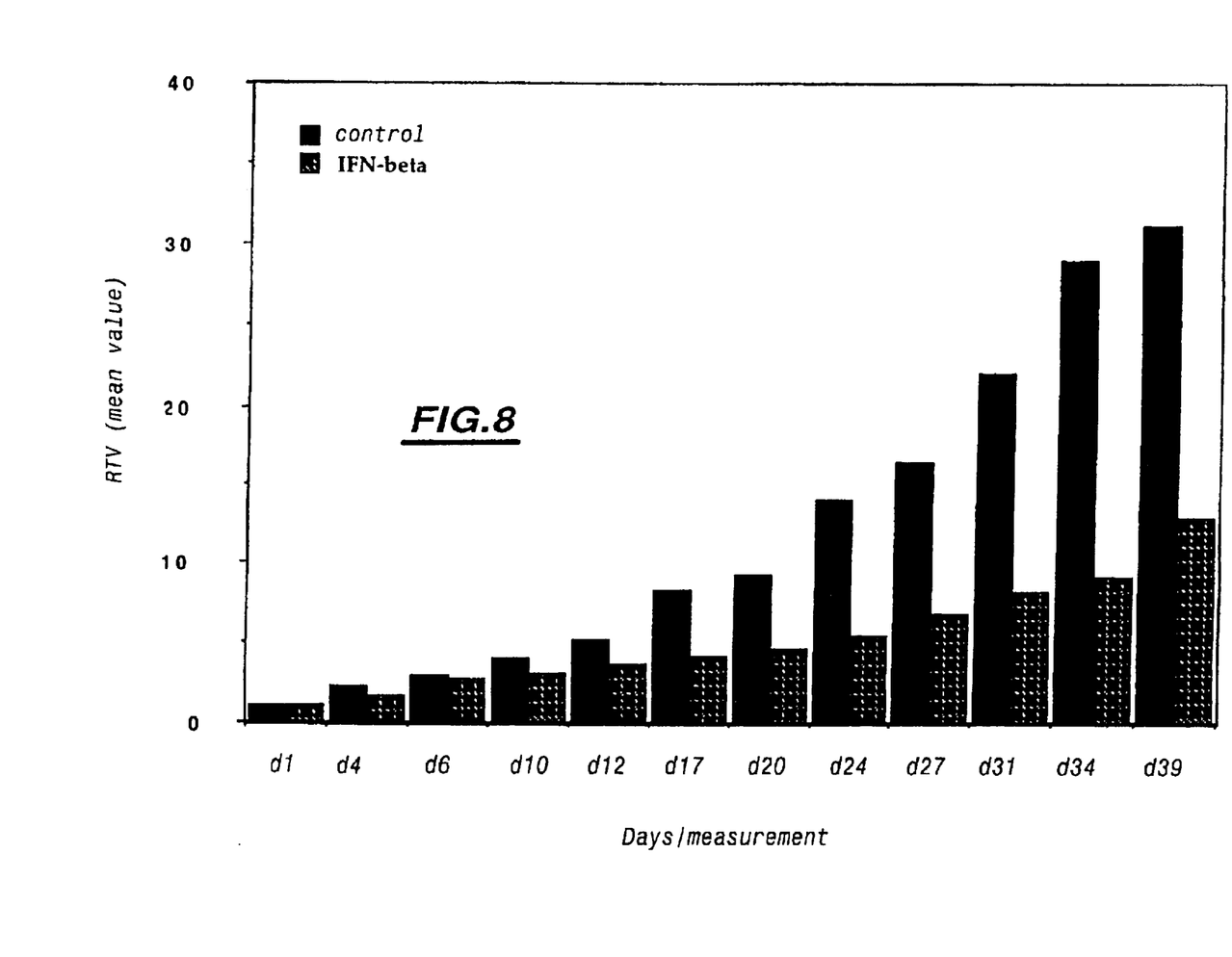
FIG. 8 and FIG. 9 show the effect of IFN-β on Ewing's tumors grown in nude mice after IFN-β injection. The average value of relative tumor volumes (RTV) of 12 mice and volume median were determined every third day.
Figure 9:
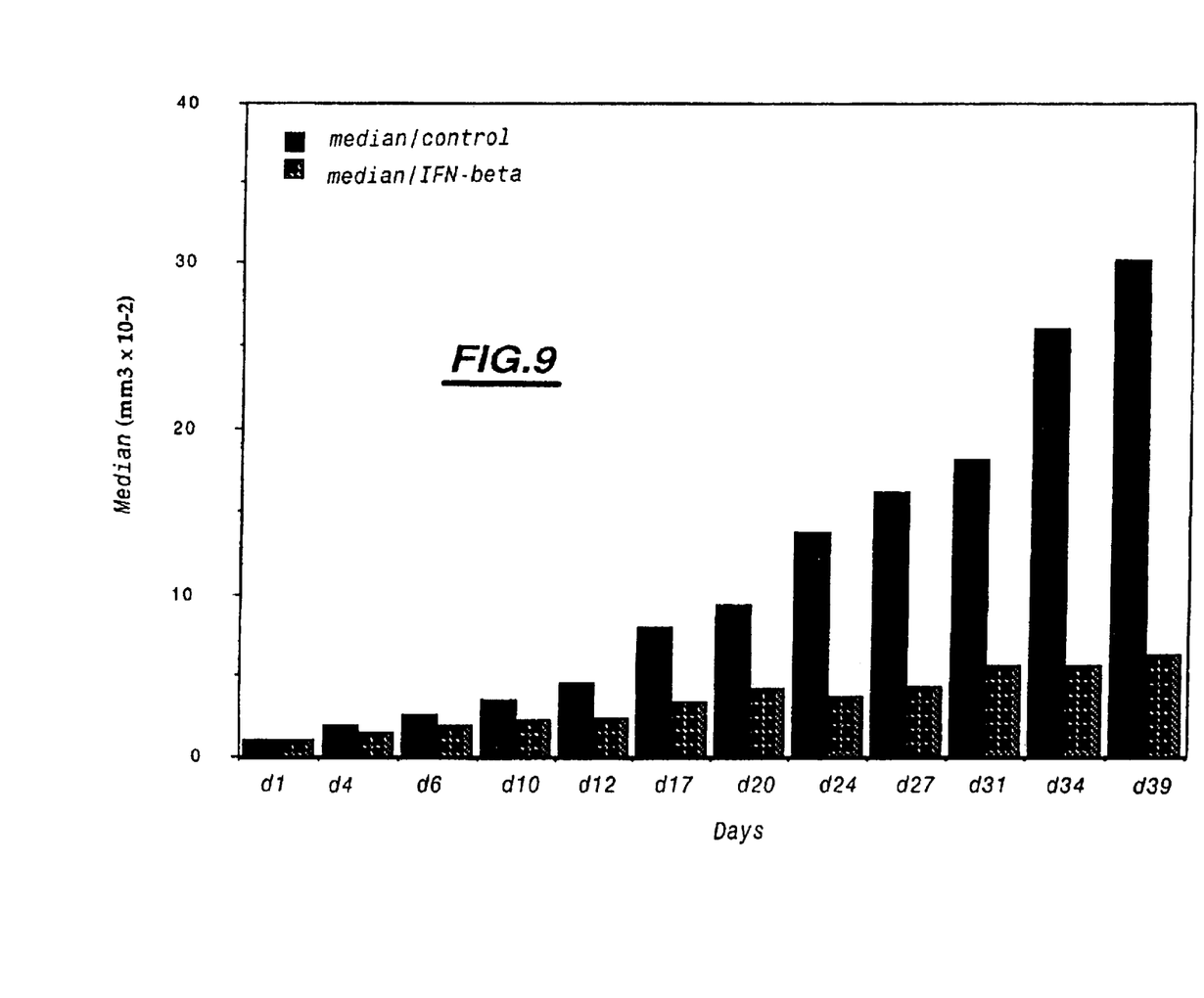

The relative volumes (RTV) and median tumor diameters defined accordingly revealed a very marked slowing of tumor development (FIG. 8 and FIG. 9).

This experiment on existent tumors at their exponential growth phase clearly showed that IFN-β has an antitumor effect on Ewing's tumor.

Example 7

Effect of the Association Chemiotherapy/IFN-β on the Growth of Ewing's Tumors in Nude Mice The effect of a chemiotherapeutic treatment with Ifosfamide, associated with IFN-β treatment on the growth of an existent Ewing's tumor in nude mice was investigated by the administration to the mice of 60 mg/kg of body weight of Ifosfamide during 3 days together with intratumoral administration of 100 000 U/day of IFN-β followed by 5 times weekly of IFN-β alone.

The growth of the Ewing's tumor was inhibited with this associated treatments, as the size of this tumor remaining stable.

Moreover, the authors have evidenced that the associated treatments have a synergic effect as said action is very higher than that resulting from independent IFN-β and Ifosfamide administration.

What is claimed is:

1. A method for the treatment of Ewing's sarcoma comprising the administration of an effective amount of interferon-beta to the mammal to treat Ewing's sarcoma.

2. A method according to claim 1, wherein the interferon-beta is recombinant.

3. A method according to claim 1, wherein the interferon-beta is 1a.

4. A method according to claim 1, wherein the interferon-beta is glycosylated.

5. A method according to claim 1, wherein the interferon-beta is administered parenterally.

6. A method according to claim 5, wherein the parenteral administration comprises the intramuscular, intravenous, subcutaneous or percutaneous administration of interferon-beta.

7. A method according to claim 1, wherein the interferon-beta is administered orally.

8. A method according to claim 1, wherein the interferon-beta is administered systematically.

9. A method according to claim 1, wherein the interferon-beta is administered directly to the tumor.

10. A method according to claim 1, wherein the interferon-beta is administered at a dose ranging from 1 to 90 million international units.

11. A method according to claim 10, wherein the interferon-beta is administered at a dose ranging from 1 to 45 million international units.

12. A method according to claim 1, wherein the interferon-beta is comprised in a pharmaceutically acceptable carrier.

13. A method according to claim 1, wherein the interferon-beta is administered simultaneously or sequentially with at least one additional agent.

14. A method according to claim 13, wherein the additional agent is Ifosfamide.

15. A method for assaying the sensitivity of cells of the Ewing's sarcoma to interferon-beta, comprising:

a) obtaining a sample of the cells;

b) cultivating the cells in vitro; and c) determining caspase-7 expression by the cells.

16. A method according to claim 15, wherein the expression of caspase-7 is determined by immunoassay.

17. A method for assaying the sensitivity of cells of the Ewing's sarcoma to interferon-beta, comprising:

obtaining a sample of the cells;

cultivating the cells in vitro; and determining caspase 7 activity in the cells.

18. A method according to claim 17, wherein the activity of caspase-7 is determined by immunoassay.

* * * * *